United States Patent
Wand et al.

[11] Patent Number: 5,525,388
[45] Date of Patent: Jun. 11, 1996

[54] DILATATION BALLOON WITH CONSTANT WALL THICKNESS

[75] Inventors: Bruce H. Wand, San Jose; Richard J. Saunders, Redwood Shores, both of Calif.

[73] Assignee: Advanced Cardiovascular Systems, Inc., Santa Clara, Calif.

[21] Appl. No.: 253,837

[22] Filed: Jun. 3, 1994

Related U.S. Application Data

[63] Continuation of Ser. No. 927,152, Aug. 7, 1992, abandoned.

[51] Int. Cl.6 .......................... A61M 25/10; B29B 11/14
[52] U.S. Cl. .................. 428/36.9; 428/36.92; 428/213; 428/542.8; 604/96; 606/192; 606/194; 138/118
[58] Field of Search ................ 428/542.8, 36.9, 428/36.92, 35.7, 213; 215/1 C; 604/96; 606/192, 194; 138/118

[56] References Cited

U.S. PATENT DOCUMENTS

| | | | |
|---|---|---|---|
| 4,490,421 | 12/1984 | Levy | 428/36.92 |
| 4,692,200 | 9/1987 | Powell | 606/192 |
| 4,715,378 | 12/1987 | Pope, Jr. et al. | 606/194 |
| 4,848,344 | 7/1989 | Sos et al. | 606/194 |
| 4,952,357 | 8/1990 | Euteneuer | 264/129 |
| 5,035,694 | 7/1991 | Kasprzyk et al. | 604/96 |
| 5,334,146 | 9/1994 | Ozasa | 606/194 |

*Primary Examiner*—Ellis P. Robinson
*Assistant Examiner*—Rena L. Dye
*Attorney, Agent, or Firm*—Crosby, Heafey, Roach & May

[57] ABSTRACT

A balloon for a dilatation catheter having a cylindrically shaped working section and tapered end sections which have essentially the same wall thicknesses. Upon deflation, the balloon collapses to a much smaller profile than conventional dilatation catheters. The balloon is preferably formed from a tubular parison which has a central thick walled portion. The balloon may be employed in dilatation catheters for angioplasty, prostatic urethra dilatations and other intraluminal dilatations.

1 Claim, 1 Drawing Sheet

DILATATION BALLOON WITH CONSTANT WALL THICKNESS

This is a continuation of application Ser. No. 07/927,152 which was filed on Aug. 7, 1992 now abandoned.

BACKGROUND OF THE INVENTION

This invention generally relates to dilatation balloons which are used on balloon dilatation catheters for percutaneous transluminal coronary angioplasty (PTCA).

In conventional PTCA procedures, a guiding catheter having a preshaped distal tip is percutaneously introduced into the cardiovascular system of a patient and advanced therein until the preshaped distal tip of the guiding catheter is disposed within the aorta adjacent the ostium of the desired coronary artery. The guiding catheter is twisted or torqued from the proximal end to turn the distal tip of the guiding catheter so that it can be guided into the coronary ostium. With over the wire dilatation catheter systems, a guidewire and a balloon dilatation catheter are introduced into and advanced through the guiding catheter to the distal tip, with the guidewire slidably disposed within an inner lumen of the dilatation catheter. The guidewire is first advanced out the distal tip of the guiding catheter, which is seated in the ostium of the patient's coronary artery, until the distal end of the guidewire crosses the lesion to be dilated. The dilatation catheter is then advanced out of the distal tip of the guiding catheter, over the previously advanced guidewire, until the balloon on the distal extremity of the dilatation catheter is properly positioned across the lesion. The balloon is then inflated to a predetermined size with radiopaque liquid at relatively high pressures (e.g., generally 4–12 atmospheres) to dilate the stenosed region of the diseased artery. After one or more inflation-deflation cycles, the balloon is finally deflated so that the dilatation catheter can be removed from the dilated stenosis and blood flow will resume through the artery.

A continual effort has been made by those skilled in the art to reduce the profile, i.e. transverse dimensions, of dilatation catheters, particularly the balloon, to enable the catheter to be advanced much further into a patient's vasculature or other body lumens and to cross much tighter or narrower lesions. In the case of balloons for prostatic urethral dilatations the reduced deflated profile of the balloon is also important to facilitate advancing and withdrawing the balloon through a conventional cystoscope.

The prior art dilatation balloons for dilatation catheters have generally been formed of relatively inelastic polymeric materials such as polyethylene, polyvinyl chloride, polyethylene terephthalate (PET) and polyolefinic ionomers. The dilatation balloons made of these materials were frequently heat formed in the deflated state so as to wrap around an inner member within the catheter in order to present as low a profile as possible. However, when the prior art balloons are deflated after being inflated, they have a tendency to form outwardly projecting wings which can interfere with the passage the deflated balloons through body lumens and particularly the stenosis to be dilatated. This is particularly true of balloons made of high strength plastic materials such as PET and Nylon. However, high strength balloon materials are preferred because these balloons can be made with much thinner walls and therefore allow for much lower profiles than balloons formed of lower strength materials. Additionally, the tapered section of the balloon for dilatation catheters generally is much thicker and therefore less flexible than the working section of the balloon. As a result the thicker section is less apt to collapse upon deflation than the working section, thereby providing a larger profile.

What has been needed and heretofore unavailable is a dilatation balloon formed of high strength polymer materials which upon deflation after inflation returns to a very low profile along the entire length of the balloon. The present invention satisfies this and other needs.

SUMMARY OF THE INVENTION

This invention is directed to a dilatation balloon which upon deflation after inflation collapses to a very low profile, a parison for making such a balloon and the method of making such a balloon.

A dilatation balloon of the invention generally has upon inflation a cylindrical working section and tapered end sections which have essentially the same wall thicknesses. The variation in wall thickness in the working and tapered sections of the balloon should not be greater than about 40%, preferably less than 20% of the nominal or average wall thickness. The wall thickness of the waist portions of the balloon which extend proximal and distal to the tapered sections generally will be larger than the wall thickness of the working and the tapered sections. The short transition between the tapered ends of the balloon and the waist portions of the balloon which increase in thickness arc significant and are ignored.

The balloon of the invention may be conveniently formed by expanding a thermoplastic tubular parison which has a tubular section with a relatively thick wall thickness which forms the working section of the balloon and tubular sections adjacent to the ends of the relatively thick wall section which taper away from the thicker tubular section to thinner wall sections and which form the tapered end sections of the balloon. When the parison is expanded by heating and introducing high pressure fluid into the interior thereof, the parison forms a balloon having an inflated working section and tapered end sections with essentially the same wall thicknesses. This results in a reduction in the maximum wall thickness of the tapered balloon portions by about 20 to about 50% over the tapered sections of conventional balloons.

Several methods may be utilized to make the tubular parison of the desired size and shape to form the balloon with an essentially constant wall thickness. The most direct way is to form a tubular member with a wall thickness the same size as that required to form the working section of the balloon and then thinning the wall of the tubular member on both sides of the portion of the tubular member which forms the working section by machining, abrading or other suitable means to form the tapered sections of the parison.

Another method is to extrude a tubular member through an extrusion die with an inner shaping member such as a mandrel disposed within the extrusion die which has a variable effective outer diameter. In this manner at the start of the extrusion the inner mandrel may be at a first outer diameter so as to provide an extruded wall section which ultimately forms the skirt or waist of the balloon. The effective outer diameter of the mandrel is then gradually reduced during the extruding process to a second outer diameter, smaller than the first outer diameter, to form the tapered section of the parison. The effective outer diameter of the mandrel is maintained at the smaller second diameter for a particular length of the extrusion to form the thick section of the parison and then the effective outer diameter of the mandrel is increased to a third diameter larger than the second diameter in order to form the other tapered section of the parison on the opposite end of the thick section. The extruding process is continued while the effective outer diameter of the mandrel is maintained in the third diameter to form the thin wall section which forms the other skirt of the balloon. The first and the third diameters may be the same. In one embodiment of the invention, the effective outer diameter of the mandrel may be varied by providing an expandable mandrel. In another embodiment a tapered mandrel is axially disposed within the extrusion die and the effective outer diameter is varied by advancing or withdrawing the tapered mandrel within the extrusion due.

Upon inflation of the above described parison at elevated temperatures by injecting high pressure fluid into the inner chamber thereof, a balloon is formed which has a cylindrically shaped working section and tapered end sections which have essentially the same wall thicknesses as the cylindrically shaped working section. A balloon with essentially constant wall thicknesses in both the working and tapered sections, particularly the tapered sections, will collapse to a very small transverse profile along its entire length when the interior of the balloon is subjected to a vacuum. These an other advantages will become more apparent from the following detailed description of the invention, particularly when taken in conjunction with the accompanying exemplary drawings

DETAILED DESCRIPTION OF THE INVENTION

Figure 1:
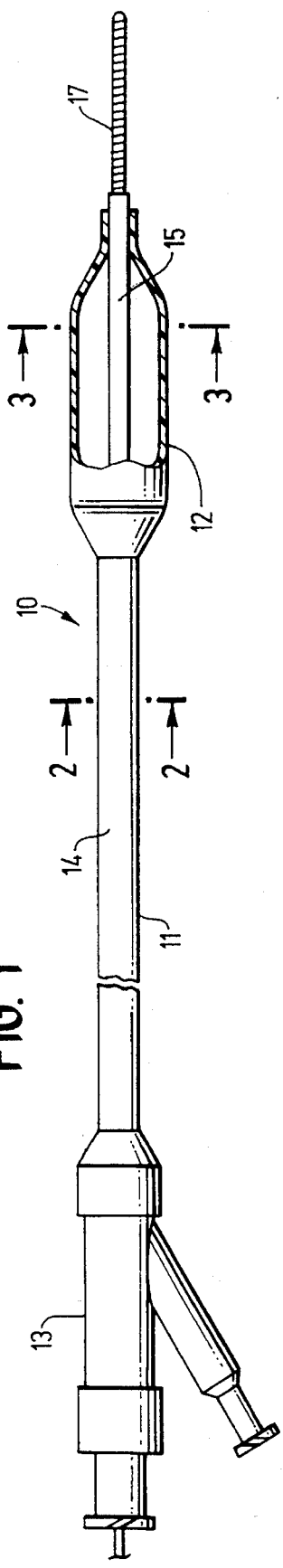
FIG. 1 is an elevational view, partially in section, of a dilatation catheter embodying features of the invention.
Figure 2:
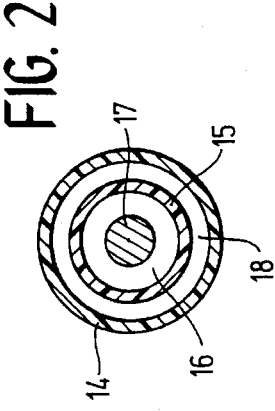
FIG. 2 is a transverse cross-sectional view of the catheter shown in FIG. 1 taken along the lines 2—2.
Figure 3:
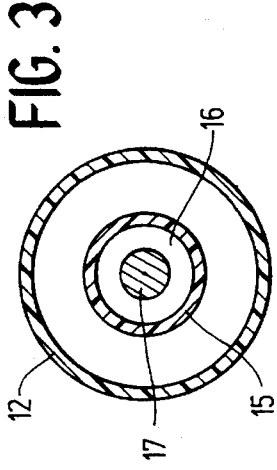
FIG. 3 is a transverse cross-sectional view of the catheter shown in FIG. 1 taken along the lines 3—3.

Reference is made to FIGS. 1—3 which illustrate an over-the-wire dilatation catheter 10 which embodies features of the invention. The dilatation catheter 10 generally includes an elongated catheter shaft 11, a balloon 12 having a relatively constant wall thickness and an adapter 13 on the proximal end of the catheter shaft 11.

The catheter shaft 11 has an outer tubular member 14 and inner tubular member 15 disposed within the outer tubular member. The inner tubular member 15 has an inner lumen 16 adapted to receive a guidewire 17. The inner tubular member 15 and the outer tubular member 14 define an annular lumen 18 which directs inflation liquid to the interior of the balloon 12.

Figure 4:
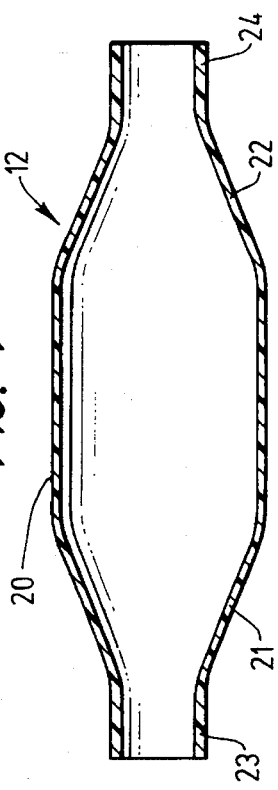
FIG. 4 is a longitudinal cross-sectional view of a balloon embodying features of the invention.

As shown more clearly in FIG. 4, the balloon 12 has an elongated cylindrically shaped working section 20 and tapered sections 21 and 22 on opposing ends of the working section. Skirts or waists 23 and 24 are provided respectively on the small diameter ends of the tapered sections 21 and 22. As illustrated in the drawings, the wall thicknesses of the working section 20 and the tapered sections 21 and 22 have essentially the same wall thickness. The skirts 23 and 24 need not and generally do not, have the same wall thickness as the tapered and working sections 20-22.

The distal skirt 24 of the balloon 12 is secured or otherwise bonded to the distal end of the inner tubular member 16 and the proximal skirt 23 may be a part of the outer tubular member 15 as shown or may be a separate member which is secured or otherwise bonded to the distal end of the outer tubular member 15.

Figure 5:
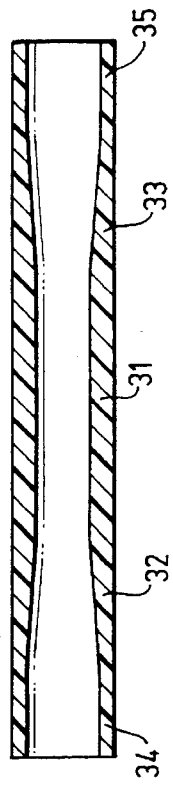
FIG. 5 is a longitudinal cross-sectional view of a parison which embodies features of the invention.

FIG. 5 is a longitudinal cross-sectional view of a parison 30 from which the balloon 12 shown in FIG. 4 can be made. In this embodiment, the parison 30 has a relatively thick middle portion 31 and end portions 32 and 33 which have tapered walls which are their thickest adjacent the middle portion thereof and which taper in a direction away from the middle portion to smaller wall thicknesses. Relatively thin tubular sections 34 and 35 of constant wall thickness which form the balloon skirts are provided adjacent the tapered end portions. Upon subjecting the parison 30 to elevated temperatures and the inflation thereof to inflation fluid at high pressures, the parison 30 expands to the balloon 12 shown in FIG. 4 with wall thicknesses in the working section 20 and the tapered sections 21 and 22 being essentially the same. The parison 30 may be blown into the balloon 12 inside a mold having an interior molding chamber of essentially the same shape as the desired shape of the balloon. The forming parameters will depend upon the polymeric material use and generally will be conventional. The thickness and length of the various portions of the parison will depend upon the size of the balloon to be formed from the parison. Typical balloon sizes include a length of working section of about 20 mm, a length of about 1.5 to about 3 mm for each of the tapered sections with the wall thicknesses thereof ranging from about 0.0002 to about 0.001 inch.

While the present invention has been described herein in terms of over-the-wire dilatation catheters for coronary angioplasty, those skilled in the art will recognize that fixed-wire, rapid exchange and other types of dilatation catheters may employ a balloon in accordance with the invention. Moreover, the balloons of the invention will be suitable for catheters for the dilatation of other body lumens such as prostatic urethras in the treatment of prostatic hyperplasia. Other modifications and improvements can be made to the invention without departing from the scope thereof.

What is claimed is:

1. A continuous expandable thermoplastic parison for blowing a dilatation balloon which has a cylindrically shaped working section and tapered tubular sections with essentially the same wall thicknesses, the parison comprising:

an elongated central tubular thick wall section of constant wall thickness which when expanded during blowing forms the cylindrically shaped working section of the balloon, a tubular section secured to each tubular of the thick wall section having decreasing wall thickness in a direction away from the thick wall section which, when expanded during blowing, forms the tapered end sections of the balloon; and a tubular thin wall open-ended section of constant thickness secured to each end of the tapered tubular sections which extend away from the thick wall section and having a constant wall thickness after the parison is blown into a balloon greater than the constant wall thickness of the tapered sections and the cylindrically shaped working tubular section.

* * * * *

UNITED STATES PATENT AND TRADEMARK OFFICE
CERTIFICATE OF CORRECTION

PATENT NO. : 5,525,388

DATED : June 11, 1996

INVENTOR(S) : Wand et al.

It is certified that error appears in the above-identified patent and that said Letters Patent is hereby corrected as shown below:

Column 4, line 52, insert --tapered-- before "tubular section";

column 4, line 52, delete the second instance of "tubular" and insert therefore --end--;

column 4, line 55, delete "end" and insert therefore --tubular--;

column 4, line 62, insert --tubular-- after "tapered".

Signed and Sealed this

Tenth Day of September, 1996

Attest:

BRUCE LEHMAN

*Attesting Officer*    *Commissioner of Patents and Trademarks*